United States Patent
Benkert et al.

(10) Patent No.: US 10,789,740 B2
(45) Date of Patent: Sep. 29, 2020

(54) METHOD FOR MR IMAGE RECONSTRUCTION AND MR SYSTEM

(71) Applicant: Siemens Healthcare GmbH, Erlangen (DE)

(72) Inventors: Thomas Benkert, Uttenreuth (DE); Marcel Dominik Nickel, Herzogenaurach (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/662,353

(22) Filed: Oct. 24, 2019

(65) Prior Publication Data
US 2020/0151919 A1 May 14, 2020

(30) Foreign Application Priority Data
Nov. 14, 2018 (DE) .................. 10 2018 219 457

(51) Int. Cl.
*G06T 11/00* (2006.01)
*G01R 33/565* (2006.01)

(52) U.S. Cl.
CPC ........ *G06T 11/005* (2013.01); *G01R 33/5659* (2013.01); *G06T 11/006* (2013.01)

(58) Field of Classification Search
CPC .. G06T 11/005; G06T 11/006; G01R 33/5659
See application file for complete search history.

(56) References Cited

U.S. PATENT DOCUMENTS

| | | | | |
|---|---|---|---|---|
| 7,218,107 B2 * | 5/2007 | Fuderer | ................ | G01R 33/565 324/309 |
| 7,514,924 B2 * | 4/2009 | Luedeke | ............ | G01R 33/3621 324/309 |
| 10,012,717 B2 * | 7/2018 | Wang | ................. | G01R 33/5611 |
| 10,126,397 B2 * | 11/2018 | Cauley | ............... | G01R 33/5608 |

(Continued)

OTHER PUBLICATIONS

German Grant Decision for German Application No. 10 2018 219 457.2. Grant decision Sep. 30, 2019, with English Translation.

(Continued)

*Primary Examiner* — Dixomara Vargas
(74) *Attorney, Agent, or Firm* — Lempia Summerfield Katz LLC

(57) ABSTRACT

Methods are provided for magnetic resonance (MR) image reconstruction. In one exemplary method, a low-resolution prescan MR data record is recorded, the prescan MR data record is adjusted to a provided form of a higher resolution scan MR data record which is likewise to be recorded, a compressed prescan MR data record is generated by geometric coil compression, the scan MR data record is recorded, a compressed scan MR data record is generated by geometric coil compression, and the compressed scan MR data record is then corrected by the compressed prescan MR data record. An MR system includes an MR coil arrangement configured to generate static and high-frequency magnetic fields at the site of an object to be examined and to detect response signals output by the object, and a data processing device configured to process data of the object generated from the response signals, wherein the data processing device is embodied to carry out the method.

14 Claims, 2 Drawing Sheets

(56) References Cited

U.S. PATENT DOCUMENTS

| | | | |
|---|---|---|---|
| 10,310,042 B2* | 6/2019 | Cauley | G01R 33/482 |
| 2007/0024281 A1* | 2/2007 | Fuderer | G01R 33/565 |
| | | | 324/309 |
| 2010/0013472 A1* | 1/2010 | Buehrer | G01R 33/3415 |
| | | | 324/307 |
| 2013/0044960 A1 | 2/2013 | Zhang | |
| 2015/0073258 A1* | 3/2015 | Mazer | G01R 33/4828 |
| | | | 600/410 |
| 2015/0323633 A1* | 11/2015 | Cauley | G01R 33/5608 |
| | | | 324/309 |
| 2016/0097831 A1 | 4/2016 | Dannels | |
| 2016/0306019 A1* | 10/2016 | Wang | G01R 33/5611 |
| 2017/0045599 A1* | 2/2017 | Cauley | G01R 33/5612 |
| 2019/0154784 A1* | 5/2019 | Polak | G01R 33/4818 |
| 2019/0346518 A1* | 11/2019 | Lingala | G01R 33/34084 |

OTHER PUBLICATIONS

German Office Action for German Application No. 10 2018 219 457.2 dated Aug. 1, 2019, with English Translation.

Zhang, Tao, et al. "Coil compression for accelerated imaging with Cartesian sampling." Magnetic resonance in medicine 69.2 (2013): 571-582.

* cited by examiner

US 10,789,740 B2

METHOD FOR MR IMAGE RECONSTRUCTION AND MR SYSTEM

The present patent document claims the benefit of German Patent Application No. 10 2018 219 457.2, filed Nov. 14, 2018, which is hereby incorporated by reference.

TECHNICAL FIELD

The disclosure relates to a method for magnetic resonance (MR) image reconstruction, with which a lower resolution prescan MR data record is recorded and is adjusted to an intended form of a higher resolution scan MR data record which is likewise to be recorded, the scan MR data record is recorded, a compressed scan MR data record is generated by geometric coil compression, and the compressed scan MR data record is then corrected by the prescan MR data record. The disclosure also relates to an MR system configured to carry out the method.

BACKGROUND

In modern magnetic resonance tomography (MRI or MR) devices, an object to be examined is excited by a combination of static and high-frequency magnetic fields and the signal output by the object as a response thereto is registered with a plurality of $N_{cr}$ different receive coils. An image reconstruction carried out within the scope of the magnetic resonance tomography may be carried out separately for each of these receive coils, and the images calculated from the respective MR data records are combined in an act to form a final image. The reconstruction which is separate for each receive coil may lead to long reconstruction times, which may be problematic in clinical practice, particularly with the use of time-consuming reconstruction techniques (such as, e.g., what is known as "compressed sensing").

In order to solve this problem, concepts were developed in the past in order to combine or "compress" the structurally present $N_{cr}$ actual coils to form a number $N_{cc}$ of what are known as virtual coils, wherein $N_{cc} < N_{cr}$.

A significantly increased compression with a consistent image quality is reached by what is known as "geometric coil compression," which is described in Zhang et al., Magn. Reson. Med., 2013, 69: 571-582, U.S. Patent Application Publication No. 2013/0044960 A1 and U.S. Patent Application Publication No. 2016/0306019 A1, for instance. In this regard, the three-dimensional measuring space volume along a predetermined fully scanned dimension (e.g., as described in U.S. Patent Application Publication No. 2016/0306019 A1 along a slice direction) is firstly decoupled into a number of two-dimensional volumes, in particular slices and/or planes. These two-dimensional volumes may be compressed separately. Significantly higher compression rates may be achieved by this spatially resolved approach, as is shown in FIG. 3 of U.S. Patent Application Publication No. 2013/0044960 A1.

What is known as a "prescan," in which a lower resolution "prescan" MR data record is recorded, is still frequently carried out before a high-resolution measuring process or "scan" is carried out. During a prescan, various calibrations and/or corrections are carried out, in order to obtain an improved recording according to a specific protocol. Acts of a prescan may include, e.g., what is known as "quick shimming," tuning and adjusting coils, adjusting the central frequency, adjusting the transmitter and receiver-side attenuation and amplification of signals, etc. Moreover, a phase correction for an adaptive-combine coil combination may be carried out by the prescan.

A previously unresolved problem with the geometric coil compression involves intensity variations and phase singularities produced by the compression of the MR data record and which may result in cancellation artifacts in the image reconstructed therefrom.

BRIEF SUMMARY AND DESCRIPTION

The scope of the present disclosure is defined solely by the appended claims and is not affected to any degree by the statements within this summary. The present embodiments may obviate one or more of the drawbacks or limitations in the related art.

It is the object of the present disclosure to at least partially overcome the disadvantages of the prior art and, in particular, to provide an option in the field of magnetic resonance tomography to suppress, in particular eliminate, intensity variations and/or phase singularities with the geometric coil compression.

The object is achieved by methods for MR image reconstruction. The methods include recording an MR data record with low resolution (referred to below without restricting generality as a "prescan MR data record); adjusting the prescan MR data record to an intended form of a higher resolution MR data record which is likewise to be recorded (referred to below without restricting generality as "scan MR data record"); generating a compressed prescan MR data record by geometric coil compression, (e.g., from the adjusted prescan MR data record); recording the scan MR data record; generating or recording a compressed scan MR data record by geometric coil compression, (e.g., from the recorded scan MR data record); and correcting the compressed scan MR data record by the compressed prescan MR data record or based on the compressed prescan MR data record.

This method is advantageous in that as a result of the compressed scan MR data record being corrected by a compressed prescan MR data record, intensity variations and/or phase singularities in the compressed scan MR data record may be reduced or even avoided entirely. In this way, the knowledge that such intensity variations and/or phase singularities have therefore previously occurred at least partially is used to full advantage because compressed scan MR data records have been corrected based on uncompressed prescan MR data records.

An MR data record may have a number of spatially distributed data points, which are also referred to below as "pixels." The pixels may be assigned in particular to a uniformly distributed pattern, which has the spatial coordinates (x, y, z) and in particular a complex value at each of these coordinates. If $N_{cr} > 1$ actually existing receive coils are used for data recording, the uncompressed MR data record ("multi-channel MR data record"), described in Cartesian coordinates, has a pixel quantity of $N_x \cdot N_y \cdot N_z \cdot N_{cr}$ pixels, wherein $N_x$ shows the number of pixels in an x-direction, $N_y$ shows the number of pixels in a y-direction and $N_z$ shows the number of pixels in a z-direction for in each case one of the actually existing coils or coils used for detection and thus shows the image resolution. The MR data record therefore corresponds to a superimposition of $N_{cr}$ partial data records of the same spatial three-dimensional measuring space volume, which are assigned to different actually existing coils, however. In other words, a value group with $N_{cr}$ individual values is assigned to a spatial pixel. Each pixel is a complex-value pixel.

In this way, the pixels of a multichannel MR data record arbitrarily select a global phase, with which all individual channel MR data records are multiplied. The prescan MR data record contains information which enables these global phases to be defined and indeed also for the scan MR data record. For instance, both at least one body coil and also at least one surface coil may be used as receive coils, wherein the global phase is only corrected based on the body coil(s). In particular, the at least one surface coil may be used for a subsequent image reconstruction, while the at least one body coil is not used in the imaging measurement.

An MR data record or its pixels may include both the information required as such for the imaging and also an item of phase information. This may also be expressed in particular in that an MR data record has the MR image and an additional item of phase information. In one development, the prescan MR data record may also presently include only the respective phase information for each pixel.

In one development, an MR data record may also presently include per pixel a respective coil sensitivity, in particular phase-corrected coil sensitivity. In the simplest case, the coil sensitivity for a coil at a specific position or at a pixel easily corresponds to the relative portion of this coil at the signal of all coils at this position or at this pixel (e.g. according to standard $1^2$).

The fact that the prescan MR data record has a low resolution includes in particular that in at least one spatial dimension it has a lower resolution or a lower number of pixels per length unit or pixel density than the scan MR data record to be corrected. A resolution may therefore be understood here in particular to mean a pixel density. It is advantageous here if a resolution of the prescan MR data record and the scan MR data record corresponds in each dimension to a power of two, in particular per detector coil.

In one development, the uncompressed prescan MR data record has a pixel quantity or a data record of:

$$Nps_x \times Nps_y \times Nps_z \times N_{cr}$$

pixels, wherein $Nps_x$ represents the number of pixels in an x-direction, $Nps_y$ represents the number of pixels in a y-direction, $Nps_z$ represents the number of pixels in a z-direction for in each case one of the actually existing coils or coils used for detection purposes and $N_{cr}$ corresponds to the number of actually existing coils. The prescan MR data record therefore corresponds in particular to a superimposition of $N_{cr}$ partial data records of the same spatial three-dimensional measuring space volume, which are assigned to different actually existing coils, however. In other words, a value group with $N_{cr}$ individual values is assigned to a spatial pixel. The uncompressed prescan MR data record has the following $Nps_x \cdot Nps_y \cdot Nps_z \times Nc_r$ pixels. Each pixel is a complex-value pixel.

The fact that the scan MR data record is a data record that is "likewise" to be recorded may include that the scan MR data record and the prescan MR data record run during a shared MR measurement sequence or MR measurement program, e.g., under the same boundary conditions as the same measurement settings, etc. During the method provision is made in particular to generate the prescan MR data record and the scan MR data record automatically within the scope of a shared program sequence.

The fact that the scan MR data record is a data record which is "likewise" to be recorded means in one development that the prescan MR data record is recorded prior to the scan MR data record in terms of time. The fact that the scan MR data record is a data record which is "likewise" to be recorded may mean, in another development, that the prescan MR data record is recorded during the recording of the scan MR data record (so-called "integrated prescan" or "integrated reference scan"). The scan MR data record and the prescan MR data record may therefore be generated during a shared measurement. In one variant, it is possible in the meantime to carry out a measurement during the measurement with the at least one body coil.

An MR image may be reconstructed from the compressed and corrected scan MR data record by known methods.

In one embodiment, the prescan MR data record is composed of a number of layers or a cohort of $Nps_z$ spatially parallel planes. The number of parallel planes may also be referred to as $N_{par}$. The scan MR data record may likewise be composed of a number of layers or a cohort of $Ns_z$ of parallel planes, wherein the number of planes may be different or the same.

In one embodiment, the fact that the act that the prescan MR data record is adjusted to an intended form of the scan MR data record means that the pixel density of the prescan MR data record is adjusted to the pixel density of the scan MR data record (which may also be referred to as acquired image resolution). This may also be expressed so that the pixel density of the original prescan MR data record, with the same absolute pixel size, is configured to the pixel density of the scan MR data record according to:

$$Nps_x \times Nps_y \times Nps_z \times N_{cr} \rightarrow Ns_x \times Ns_y \times Ns_z \times N_{cr}$$

wherein $Ns_x$ represents the number of pixels in a x-direction with an acquired image resolution, $Ns_y$ represents the number of pixels in a y-direction with an acquired image resolution and $Ns_z$ represents the number of pixels in a z-direction with an acquired image resolution. In particular, $Ns_x > Nps_x$ and/or $Ns_y > Nps_y$ and/or $Ns_z > Nps_z$ may apply. To implement this embodiment, the prescan MR data record may be In one embodiment, the act that the prescan MR data record is adjusted to an intended form of a three-dimensional scan MR data record means that the prescan MR data record is tailored to the same, in particular spatially three-dimensional field of view (FOV), as the scan MR data record which is likewise to be recorded. As a result, artifacts are avoided as a result of different fields of view.

The prescan MR data record therefore corresponds in terms of resolution and spatial extent to the scan MR data record. This is advantageous in that a link, (e.g., correction), of the scan MR data record with the prescan MR data record may be carried particularly easily pixel-by-pixel.

The correction of the scan MR data record with the prescan MR data record adjusted and tailored to the acquired pixel density nevertheless takes place based on the compressed data records, so that they were previously subjected to the same geometric coil compression. This may be implemented particularly easily, because the prescan MR data record corresponds to the scan MR data record in terms of resolution and spatial extent.

With the geometric coil compression of the prescan MR data record, the data record of the prescan MR data record adjusted and tailored to the acquired pixel density is converted according to:

$$Nps_x \times Nps_y \times Nps_z \times N_{cr} \rightarrow Nps_x \times Nps_y \times Nps_z \times N_{cc}$$

wherein the number of pixels $Nps_x$, $Nps_y$ and $Nps_z$ now refers to the prescan MR data record adjusted and tailored to the acquired pixel density, $N_{cc}$ represents the number of resultant compressed coils and $N_{cc} < N_{cr}$ applies.

The geometric coil compression of the scan MR data record takes place similarly to the geometric coil compression of the prescan MR data record.

In one embodiment, the compressed scan MR data record is phase-corrected by the compressed prescan MR data record. This may be carried out in particular so that the compressed scan MR data record is phase-corrected pixel-by-pixel according to:

$$V_{sc\_korr\_ph,i} = V_{sc,i} \cdot e^{-i\alpha}$$

wherein $V_{s\_korr\_ph,i}$ corresponds to a corrected $i^{th}$ pixel of the compressed scan MR data record, $V_{sc,i}$ corresponds to a corresponding $i^{th}$ pixel of the uncorrected compressed scan MR data record and $\alpha$ corresponds to a phase angle of the corresponding $i^{th}$ pixel of the compressed prescan MR data record. An $i^{th}$ pixel has the coordinates $\{x, y, z, N_{cc}\}$.

In one embodiment, pixel-dependent coil sensitivities are determined from the scan MR data record before or after geometric coil compression and these coil sensitivities are phase-corrected with the aid of the corresponding (as yet uncompressed or compressed) prescan MR data record. A particularly effective image correction is therefore enabled. The pixel-dependent coil sensitivities of the scan MR data record may be multiplied in particular, similarly to above, pixel-by-pixel with the factor $\exp(-i \cdot \alpha)$.

In one embodiment, the compressed scan MR data record is intensity-corrected by the compressed prescan MR data record. This may be carried out so that the compressed scan MR data record is intensity-corrected pixel-by-pixel according to:

$$V_{sc\_korr\_int,i} = V_{sc,i}/B$$

wherein $V_{sc\_korr\_ph,i}$ corresponds to an intensity-corrected $i^{th}$ pixel of the compressed scan MR data record, $V_{sc,i}$ corresponds to a corresponding $i^{th}$ pixel of the uncorrected compressed scan MR data record and B corresponds to an intensity factor which in one development may be calculated according to:

$$B = \sum_i |V_{psc,i}|$$

wherein $V_{psc,i}$ corresponds to an $i^{th}$ pixel of the compressed prescan MR data record and wherein the number $N_{cc}$ of compressed coils is also totaled.

In an alternative development, the intensity factor is calculated according to the $l^2$ standard as:

$$B = \sqrt{\sum_i |V_{psc,i}|^2}$$

The object is also achieved by an MR system, at least having one MR coil arrangement, which is designed to generate static and high-frequency magnetic fields at the site of an object to be examined and to detect response signals output by the object, and a data processing device, which is designed to process data of the object generated from the response signals, wherein the data processing device for carrying out the method is described as above. The MR system may be embodied similarly to the method and has the same advantages.

The receive coils may include receive coils, body coils, etc., installed fixedly in the device.

The data processing device may be a dedicated, in particular device-specific data processing device. It may run on a server, in particular a network server, and/or as a so-called cloud-based application.

BRIEF DESCRIPTION OF THE DRAWINGS

The above-described properties, features, and advantages of this disclosure and the manner in which these are achieved will now be described more clearly and intelligibly in conjunction with the following schematic description of an exemplary embodiments, which will be described in detail with reference to the drawings.

DETAILED DESCRIPTION

Figure 1:
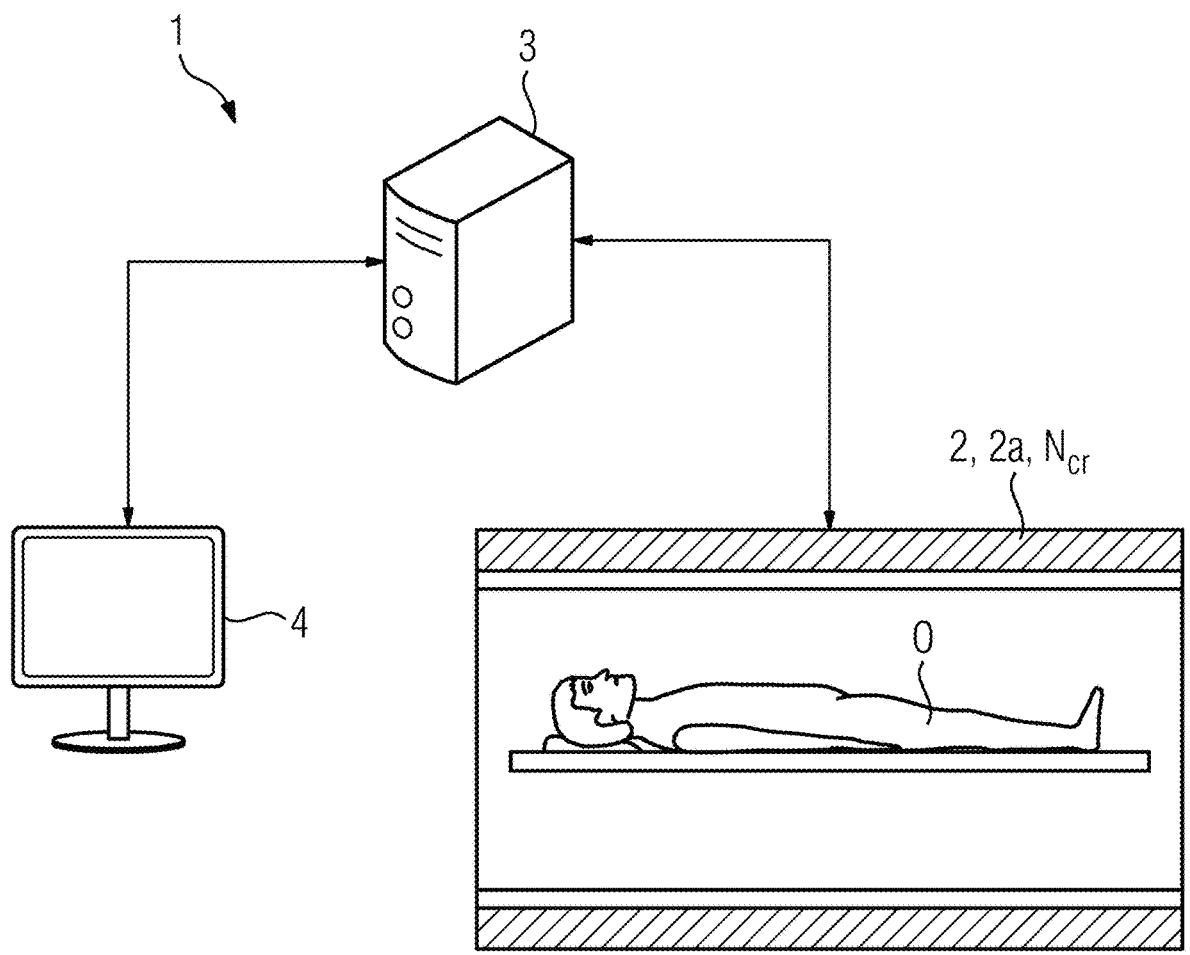
FIG. 1 depicts an example of a system which is designed to carry out the method from FIG. 1.

FIG. 1 depicts an MR system 1 with a coil arrangement 2. The coil arrangement 2 is designed to generate static and high-frequency magnetic fields at the site of an object O to be examined and to detect response signals output by the object O. In particular, the coil arrangement 2 may have $N_{cr}$ detector coils 2a.

The MR system 1 further has a data processing device 3, which is configured to process data of the object O generated from the response signals, in particular to reconstruct a three-dimensional MR image. The data processing device 3 may also be configured to prepare the MR image according to user wishes (e.g., to represent certain sectional planes etc.) and e.g. also to represent a monitor 4. One such MR system 1 is in principle well-known and is therefore not explained in more detail here.

Figure 2:
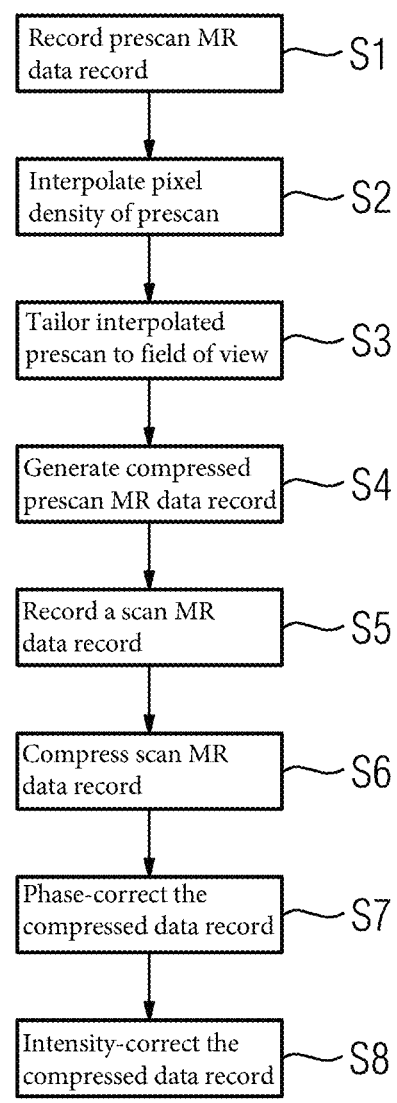
FIG. 2 depicts an example of a possible flow chart of the method.

FIG. 2 depicts a possible flow chart of the method for MR image reconstruction.

In act S1, the MR system 1 is used for instance to record a spatial three-dimensional prescan MR data record with for instance $Nps_x \times Nps_y \times Nps_z \times N_{cr} = 64 \times 64 \times 64 \times N_{cr}$ pixels or pixels per length unit (e.g., cm), wherein the prescan MR data record may be combined in particular from $N_{par} = N_{cr} = 64$ parallel planes.

In act S2, the pixel density of the prescan MR data record is interpolated with the acquired pixel density or resolution of the scan MR data record to be corrected, wherein the acquired pixel density may in each case may lie between 128 and 512 pixels per length unit (in other words two to eight times higher than the pixel density of the originally recorded prescan MR data record), but is not restricted thereto.

In act S3, the previously interpolated prescan MR data record is tailored to the field of view of the scan MR data record to be corrected.

In act S4, a compressed prescan MR data record is generated by geometric coil compression from the previously interpolated and tailored prescan MR data record, as a result of which the number of coils reduces from $N_{cr}$ to $N_{cc}$ with $N_{cc} < N_{cr}$ and the compressed prescan MR data record consequently has $N_{cc}/N_{cr}$ less pixels than the corresponding uncompressed prescan MR data record.

In act S5, the MR system 1 (in particular, under the same boundary conditions as for the prescan MR data record) is used to record a scan MR data record, which has the same relative pixel density (the acquired pixel density or image resolution) and the same field of view as the interpolated and tailored prescan MR data record.

In act S6, the scan MR data record is converted by analogue geometric coil compression like in the prescan MR data record into a compressed scan MR data record.

In act S7, the compressed scan MR data record is phase-corrected pixel-by-pixel by the compressed prescan MR data record according to:

$$V_{sc\_korr\_ph,i} = V_{sc,i} \cdot e^{-i\alpha}$$

wherein $V_{sc\_korr\_ph,i}$ corresponds to a corrected $i^{th}$ pixel of the compressed scan MR data record, $V_{sc,i}$ corresponds to a corresponding $i^{th}$ pixel of the uncorrected compressed scan MR data record and $\alpha$ corresponds to a phase angle of the corresponding $i^{th}$ pixel of the compressed prescan MR data record. This is possible because the pixels are complex pixels.

In act S8, the phase-corrected scan MR data record is intensity-corrected pixel-by-pixel by the compressed prescan MR data record according to:

$$V_{sc\_korr\_int,i} = V_{sc\_korr\_ph,i}/B$$

wherein $V_{sc\_korr\_int,i}$ corresponds to an intensity-corrected and previously phase-corrected $i^{th}$ pixel of the compressed scan MR data record and B corresponds to an intensity factor, which is calculated according to:

$$B = \sum_i |V_{psc,i}|$$

wherein $V_{psc,i}$ is also totaled across all compressed coils $N_{cc}$.

The corrected, compressed scan MR data record may then be used as a basis for display on the monitor 4.

The above acts may be carried out for each MR scan, e.g., that a prescan may be carried out prior to each scan or during each scan.

The geometric coil compression may be applied in any directions, in the case of Cartesian measurements in particular also in the fully scanned so-called "read out" direction.

The present disclosure is not restricted to the exemplary embodiment shown.

The sequence of acts is therefore not restricted to the example cited. For instance, acts S7 and S8 may also be carried out in a different sequence. If the phase correction is firstly carried out in act S7 as shown in the exemplary embodiment, in act S8 the intensity correction may be carried out based on the previously phase-corrected pixels. If, conversely, the intensity correction is firstly carried out in act S7, in act S8 the phase correction may be carried out based on the previously intensity-corrected pixels. Acts S7 and S8 may also be combined in one single act, in which the compressed scan MR data record is corrected pixel-by-pixel by the compressed prescan MR data record according to:

$$V_{sc\_korr\_ph,i} = V_{sc,i} \cdot e^{-i\alpha}/B.$$

Furthermore, it is only act S7 and not act S8 that needs to be carried out (it is therefore possible to dispense with act S8) or vice versa.

In general, "a," "an," etc., may be understood as singular or plural, in particular in the sense of "at least one" or "one or more," etc., provided this is not explicitly excluded, e.g. by the expression "exactly one," etc.

A numerical value may also include the given value as a tolerance range, provided this is not explicitly excluded.

Although the disclosure has been illustrated and described in greater detail by the exemplary embodiments, the disclosure is not restricted by the disclosed examples and other variations may be derived herefrom by the person skilled in the art without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for magnetic resonance (MR) image reconstruction, the method comprising:
   recording, by a MR system, a low-resolution prescan MR data record;
   adjusting, by a data processing device, the low-resolution prescan MR data record to an intended form of a higher resolution scan MR data record to be recorded;
   generating, by the data processing device, a compressed prescan MR data record by geometric coil compression;
   recording, by the MR system, the higher resolution scan MR data record;
   generating, by the data processing device, a compressed scan MR data record by geometric coil compression of the higher resolution scan MR data record; and
   correcting, by the data processing device, the compressed scan MR data record by the compressed prescan MR data record.

2. The method of claim 1, wherein the compressed scan MR data record is phase-corrected by the compressed prescan MR data record.

3. The method of claim 2, wherein the compressed scan MR data record is phase-corrected pixel-by-pixel by the compressed prescan MR data record according to:

$$V_{sc\_korr\_ph,i} = V_{sc,i} \cdot e^{-i\alpha}$$

wherein:
   $V_{sc\_korr\_ph,i}$ corresponds to a phase-corrected corrected $i^{th}$ pixel of the compressed scan MR data record,
   $V_{sc,i}$ corresponds to a corresponding uncorrected $i^{th}$ pixel of the compressed scan MR data record, and
   $\alpha$ corresponds to a phase angle of the corresponding $i^{th}$ pixel of the compressed prescan MR data record.

4. The method of claim 3, further comprising:
   determining coil sensitivities from the higher resolution scan MR data record; and
   phase-correcting the coil sensitivities with aid of the prescan MR data record.

5. The method of claim 4, wherein the compressed scan MR data record is intensity-corrected by the compressed prescan MR data record.

6. The method of claim 5, wherein the compressed scan MR data record is intensity-corrected pixel-by-pixel by the compressed prescan MR data record according to:

$$V_{sc\_korr\_int,i} = V_{sc,i}/B$$

wherein:

$V_{sc\_korr\_int,i}$ corresponds to an intensity-corrected $i^{th}$ pixel of the compressed scan MR data record, $V_{sc,i}$ corresponds to a corresponding uncorrected $i^{th}$ pixel of the compressed scan MR data record, and B corresponds to an intensity factor, which is calculated according to:

$$B = \sum_i |V_{psc,i}|$$

or according to:

$$B = \sqrt{\sum_i |V_{psc,i}|^2}$$

wherein $V_{psc,i}$ corresponds to a corresponding $i^{th}$ pixel of the compressed prescan MR data record.

7. The method of claim 1, further comprising:
determining coil sensitivities from the higher resolution scan MR data record; and
phase-correcting the coil sensitivities with aid of the prescan MR data record.

8. The method of claim 1, wherein the compressed scan MR data record is intensity-corrected by the compressed prescan MR data record.

9. The method of claim 8, wherein the compressed scan MR data record is intensity-corrected pixel-by-pixel by the compressed prescan MR data record according to:

$$V_{sc\_korr\_int,i} = V_{sc,i}/B$$

wherein:

$V_{sc\_korr\_int,i}$ corresponds to an intensity-corrected $i^{th}$ pixel of the compressed scan MR data record, $V_{sc,i}$ corresponds to a corresponding uncorrected $i^{th}$ pixel of the compressed scan MR data record, and B corresponds to an intensity factor, which is calculated according to:

$$B = \sum_i |V_{psc,i}|$$

or according to :

$$B = \sqrt{\sum_i |V_{psc,i}|^2}$$

wherein $V_{psc,i}$ corresponds to a corresponding $i^{th}$ pixel of the compressed prescan MR data record.

10. A method for magnetic resonance (MR) image reconstruction, the method comprising:
recording, by a MR system, a low-resolution prescan MR data record;
adjusting, by a data processing device, the low-resolution prescan MR data record to an intended form of a higher resolution scan MR data record to be recorded;
generating, by the data processing device, a compressed prescan MR data record by geometric coil compression;
recording, by the MR system, the higher resolution scan MR data record;
generating, by the data processing device, a compressed scan MR data record by geometric coil compression of the higher resolution scan MR data record; and
correcting, by the data processing device, the compressed scan MR data record by the compressed prescan MR data record,
wherein, in the adjusting, the low-resolution prescan MR data record is adjusted to a pixel density of the higher resolution scan MR data record.

11. The method of claim 10, wherein, in the adjusting, the low-resolution prescan MR data record is tailored to a same field of view as the higher resolution scan MR data record.

12. The method of claim 1, wherein, in the adjusting, the low-resolution prescan MR data record is tailored to a same field of view as the higher resolution scan MR data record.

13. The method of claim 1, wherein the higher resolution scan MR data record and the low-resolution prescan MR data record are each composed of a number of layers of two-dimensional image planes.

14. A magnetic resonance (MR) system comprising:
a MR coil arrangement configured to generate static and high-frequency magnetic fields at a site of an object to be examined and to detect response signals output by the object; and
a data processing device configured to process data of the object generated from the response signals,
wherein MR system or the data processing device is configured to:
record a low-resolution prescan MR data record;
adjust the low-resolution prescan MR data record to an intended form of a higher resolution scan MR data record to be recorded;
generate a compressed prescan MR data record by geometric coil compression;
record the higher resolution scan MR data record;
generate a compressed scan MR data record by geometric coil compression of the higher resolution scan MR data record; and
correct the compressed scan MR data record by the compressed prescan MR data record to provide a corrected compressed scan MR data record.

* * * * *